US008422697B2

(12) United States Patent
Christoph

(10) Patent No.: US 8,422,697 B2

(45) Date of Patent: Apr. 16, 2013

(54) BACKGROUND NOISE ESTIMATION

(75) Inventor: Markus Christoph, Straubing (DE)

(73) Assignee: Harman Becker Automotive Systems GmbH, Karlsbad (DE)

( * ) Notice: Subject to any disclaimer, the term of this patent is extended or adjusted under 35 U.S.C. 154(b) by 590 days.

(21) Appl. No.: 12/718,473

(22) Filed: Mar. 5, 2010

(65) Prior Publication Data

US 2010/0226501 A1 Sep. 9, 2010

(30) Foreign Application Priority Data

Mar. 6, 2009 (EP) .................................... 09154541

(51) Int. Cl.
*H04B 15/00* (2006.01)
*A61F 11/06* (2006.01)

(52) U.S. Cl.
USPC ........ 381/94.1; 381/71.1; 381/94.2; 381/94.3

(58) Field of Classification Search .................... 381/58, 381/71.1, 71.2, 94.1, 94.2, 94.3
See application file for complete search history.

(56) References Cited

U.S. PATENT DOCUMENTS

| | | | | |
|---|---|---|---|---|
| 6,263,307 | B1 | 7/2001 | Arslan et al. | |
| 7,177,805 | B1 | 2/2007 | Oh et al. | |
| 7,454,332 | B2 * | 11/2008 | Koishida et al. .............. | 704/227 |
| 2008/0140396 | A1 | 6/2008 | Grosse-Schulte et al. | |

OTHER PUBLICATIONS

Arslan et al., "New Methods for Adaptive Noise Suppression", IEEE, 1995, p. 812-815.

* cited by examiner

*Primary Examiner* — Duc Nguyen
*Assistant Examiner* — George Monikang
(74) *Attorney, Agent, or Firm* — O'Shea Getz P.C.

(57) ABSTRACT

In a system for estimating the power spectral density of acoustical background noise when the level of a smoothed power spectral density signal increases, an increment value is increased, starting from a minimum increment value, by a predetermined amount until a maximum increment value is reached if at the same time the value of the power spectral density currently determined in a new calculation cycle is larger than the estimate value of the power spectral density of the background noise determined in the previous calculation cycle. For cases in which the level of the smoothed power spectral density decreases, the amplitude of the decrement value is increased, starting from a minimum decrement value, by a predetermined amount until a maximum decrement value is reached if at the same time the value of the power spectral density currently determined in a new calculation cycle is smaller than the estimate value of the power spectral density of the background noise determined in the previous calculation cycle.

18 Claims, 8 Drawing Sheets

BACKGROUND NOISE ESTIMATION

CLAIM OF PRIORITY

This patent application claims priority from European Patent Application No. 09 154 541.8 filed on Mar. 6, 2009, which is hereby incorporated by reference in its entirety.

FIELD OF TECHNOLOGY

The invention relates for estimating background audio noise and, in particular, for estimating the background noise during simultaneous speech activity.

RELATED ART

Sound waves that do not contribute to the information content of a receiver, and are, thus, regarded as disturbing, are generally referred to as background noise. The evolution process of background noise can be typically classified in three different stages. These are the emission of the noise by one or more sources, the transfer of the noise, and the reception of the noise. It is evident that an attempt is to be made to first suppress noise signals, such as background noise, at the source of the noise itself, and subsequently by repressing the transfer of the signal. However, the emission of noise signals cannot be reduced to the desired level in many cases because, for example, the sources of ambient noise that occur spontaneously with respect to time and location can only be inadequately controlled or not at all.

A typical example of the occurrence of unwanted background noise is the use of a hands free telephone in the passenger area of an automobile. Generally, the term "background noise" used in such cases includes both external influential sound (e.g., ambient noise or noise perceived in the passenger area of an automobile) and sound caused by mechanical vibrations (e.g., in the passenger area or transmission system of an automobile). If these signals are not desired, they are referred to as noise. Whenever music or voice signals are transmitted through an electro-acoustic system in a noisy environment, such as in the interior of an automobile, the quality or comprehensibility of the signals usually deteriorate due to the background noise. The background noise can be caused by external noise sources, e.g., the wind, the engine, tires, fan and other power units in the vehicle. It is therefore directly related to the speed, road conditions and operating states in the automobile.

In order to reduce noise signals including background noise, and thus improve the subjective quality and comprehensibility of the voice signal being transferred, noise reduction systems are implemented. Known systems may operate in the frequency domain on the basis of the estimated power spectrum of the noise signal. The disadvantage of this approach is that if a voice signal occurs at the same time, its spectral information is initially included in the estimate of the power spectral density. As a result, not only is the background noise signal reduced in the subsequent filtering circuit, but also the voice signal itself is reduced. To prevent this, known methods, such as voice detection, are employed to avoid an unwanted reduction in the voice signal. However, the implementation outlay for such methods is unattractively high.

In another known method, the power spectral density is estimated using a smoothing filter without any voice detection. Here, advantage is taken of the fact that the timing characteristics of the level of voice signals typically differs significantly from the level characteristic of background noise. This is particularly due to the aspect that the dynamics of the change in level of voice signals is greater and takes place in much shorter intervals than typical changes in level of background noise. The known algorithm therefore uses constant, permanently defined small increments or decrements in comparison to the level dynamics of voice signals in order to approximate the estimated power spectral density of the background noise to the actual level of the power spectral density whenever the level of the background noise changes. Therefore, level changes in the voice signal occurring within short periods do not have any undesirable, corrupting effect on the estimate of the power spectral density of the background noise in comparison to the method mentioned above.

The disadvantage of this method, however, is that due to its slow response the described algorithm takes too long to, for example, raise the level of the estimated power spectral density to an actual high value if a previously low level of the power spectral density of the background noise spectrum was detected, i.e., if the level of the background noise rises fast and continuously over a relatively short period. The same applies in the case that a large estimated value for the level of the power spectral density of the background noise was previously determined and the algorithm has to reproduce a relatively fast drop in the value of the level of the power spectral density of the background noise, i.e., a fast, continuous reduction in level of the background noise within a short period of time.

The sluggishness of the algorithm is due to the fact that the increments or decrements in the control time constants of the algorithm have to be sufficiently small for the approximation of the estimated power spectral density of the background noise to the actual level of the power spectral density of the background noise. This is to prevent an undesirable dependency between the estimate of the power spectral density and a voice signal that occurs at the same time. The described algorithm does not respond fast enough to large continuous changes in the level of the background noise occurring within a relatively short period of time. Particularly it does not respond fast enough to large rises in level over brief periods such as can be experienced in background noise in the passenger section of an automobile.

There is a need to estimate the power spectral density of background noise responds with satisfactory speed to changes in the level of the background noise occurring within short periods of time (particularly regarding short-lived large rises in the background noise).

SUMMARY OF THE INVENTION

A system for estimating the power spectral density of acoustical background noise comprises a sensor unit for generating a noise signal representative of the background noise, and a power spectral density calculation unit that determines the current power spectral density from the noise signal by deploying consecutive calculation cycles and provides a corresponding power spectral density output signal. A time domain signal smoothing unit receives and smoothes the power spectral density output signal in the time domain, and provides a timely smoothed signal. A frequency domain signal smoothing unit receives and adapts the timely smoothed signal unit in the frequency domain, and provides smoothed power spectral density signal. An increment calculation unit calculates an increment depending on an estimate value of the power spectral density of the background noise. A decrement calculation unit calculates a decrement depending on the estimate value of the power spectral density of the background noise, and an estimate signal smoothing unit calculates the estimate value of the power spectral density of the background noise from the increments and decrements. For cases in which the level of the smoothed power spectral density signal increases, the increment value is increased, starting from a minimum increment value, by a predetermined amount until a maximum increment value is reached if at the same time the value of the power spectral density currently determined in a new calculation cycle is larger than the estimate value of the power spectral density of the background noise determined in the previous calculation cycle. For cases in which the level of the smoothed power spectral density falls, the decrement value is increased, starting from a minimum decrement value, by a predetermined amount until a maximum decrement value is reached if at the same time the value of the power spectral density currently determined in a new calculation cycle is smaller than the estimate value of the power spectral density of the background noise determined in the previous calculation cycle.

DESCRIPTION OF THE DRAWINGS

The invention can be better understood with reference to the following drawings and description. The components in the FIGs. are not necessarily to scale, instead emphasis being placed upon illustrating the principles of the invention. Moreover, in the figures, like reference numerals designate corresponding parts. In the drawings.

DETAILED DESCRIPTION

Figure 1:
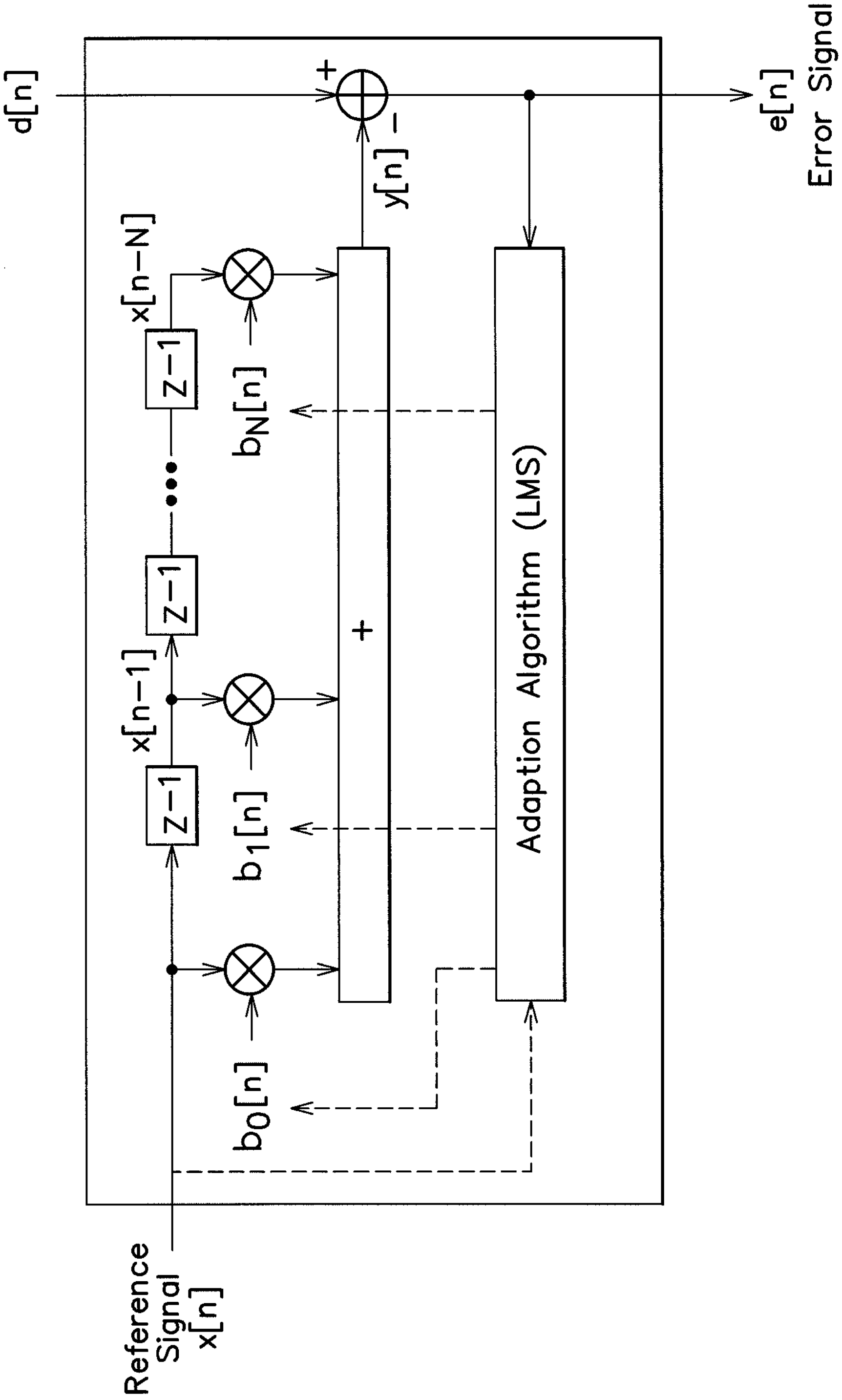
FIG. 1 is a block diagram illustration of an adaptive filter using a Least Mean Square (LMS) algorithm.

In the examples disclosed below, the power spectral density of the background noise is estimated directly from a microphone signal or from an error signal of an adaptive filter. Adaptive methods and systems have the advantage that the algorithms are adapted automatically for constant modification of their filter coefficients to changing ambient conditions, for example, to changing noise signals subject to changes in their levels and spectral composition over time. This ability is provided, e.g., by a system structure that continually optimizes the parameters. In such system, an input sensor (e.g., a microphone) is used to obtain a signal representing the unwanted noise (e.g., background noise) that is generated by one or more noise sources. The signal is then routed to the input of an adaptive filter and processed by the filter to an output signal, which is subtracted from a useful signal (e.g., a voice signal) upon which the unwanted noise signal is imposed, wherein the correlation between the input signal of the adaptive filter and the unwanted noise occurring together with the useful signal. The output signal obtained from the subtraction is also referred to as the error signal in relation to the adaptive filtering. Together with the signal of the input sensor representing the unwanted noise, the error signal forms the basis for modification of the parameters and the characteristics of the adaptive filter in order to adaptively minimize the overall level of the observed echo.

The adaptive algorithms used may be variations of the so-called Least Mean Square (LMS) algorithm as, for example, Recursive Least Squares, QR Decomposition Least Squares, Least Squares Lattice, QR Decomposition Lattice or Gradient Adaptive Lattice, Zero Forcing, Stochastic Gradient, etc. The LMS algorithm used commonly in conjunction with adaptive filters represents an algorithm for approximation of the solution of the familiar Least Mean Square problem as often encountered during implementation of adaptive filters. The algorithm is based on the so-called method of the steepest descent (falling gradient method) and estimates the gradient in a simple manner. The algorithm functions recursively in time, in other words, the algorithm is run for each new data set and the solution is updated. The LMS algorithm offers a low level of complexity and low computing power requirements, in addition to its numerical stability and low memory requirements.

Infinite Impulse Response (IIR) filters or Finite Impulse Response (FIR) filters are commonly used as adaptive filter structures. FIR filters have the properties of having a finite impulse response, which makes them absolutely stable. An nth-order FIR filter is defined by the following differential equation:

$$y(n) = b_0 * x(n) + b_1 * x(n-1) + b_2 * x(n-2) + \dots + b_N * x(n-N)$$
$$= \sum_{i=0}^{N} b_i * x[n-i]$$

where y(n) is the initial value at the time n, and is computed from the sum of the last N sampled input values x(n−N) to x(n) weighted with the filter coefficients $b_i$. The desired transfer function is realized by definition of the filter coefficients $b_i$.

Unlike FIR filters, initial values that have already been computed are also included in the computation using IIR filters (recursive filters). Such filters have an infinite impulse response. Since the computed values are very small after a finite time, the computation can in practice be terminated after a finite number of sample values n. The equation governing an IIR filter is as follows:

$$y(n) = \sum_{i=0}^{N} b_i * x(n-i) - \sum_{i=0}^{M} a_i * y(n-i)$$

where y(n) is the initial value at the time n, and is computed from the sum of the sampled input values x(n) weighted with the filter coefficients $b_i$ and added to the sum of the output values y(n) weighted with the filter coefficients The desired transfer function is realized by definition of the filter coefficients $a_i$ and $b_i$. IIR filters can be unstable in comparison to FIR filters, but have greater selectivity for the realization with the same amount of work. In practice, the filter that best fulfills the relevant requirements under consideration of the respective conditions and associated outlay will be chosen.

FIG. 1 is a block diagram illustration of a typical LMS algorithm for the iterative adaptation of an exemplary FIR filter. An input signal x[n] is chosen as the reference signal for the adaptive LMS algorithm and the signal d[n] is taken as a second input signal. The signal d[n] is derived from input signal x[n] by filtering with a transfer function of an unknown system which is superimposed by background noise and apt to be approximated by the adaptive filter. These input signals may be acoustic signals which are converted into electric signals by microphones, for example. Likewise, however, these input signals may be or include electric signals that are generated by sensors for accommodating mechanical vibrations or also by revolution counters.

FIG. 1 illustrates a FIR filter of N-th order with which the input signal x[n] is converted into the signal y[n] over discrete time n. The N coefficients of the filter are identified with $b_0[n]$, $b_1[n]$ . . . $b_N[n]$. The adaptation algorithm iteratively changes the filter coefficients $b_0[n]$, $b_1[n]$ . . . $b_N[n]$ until an error signal e[n] which is the difference signal between the signal d[n] and the filtered input signal y[n] (output signal) is minimal. The signal d[n] is the input signal x[n] distorted by the unknown system which, in addition also includes background noise, if present.

Generally, both of the signals x[n] and d[n] input into the adaptive filter are stochastic signals. In case of an acoustic echo cancellation system, they are noisy measuring signals, audio signals or communications signals, for example. The output of the error signal e[n] and the mean error square, the so-called mean squared error (MSE), is thus often used as quality criterion for the adaptation, where:

$$MSE=E\{e^2[n]\}.$$

The quality criterion expressed by the MSE can be minimized by a simple recursive algorithm, such as the known least mean square (LMS) algorithm. With the least mean square method, the function to be minimized is the square of the error. That is, to determine an improved approximation for the minimum of the error square, only the error itself, multiplied with a constant, must be added to the last previously-determined approximation. The adaptive FIR filter must thereby be chosen to be at least as long as the relevant portion of the unknown impulse response of the unknown system to be approached, so that the adaptive filter has sufficient degrees of freedom to actually minimize the error signal e[n].

The filter coefficients are gradually changed in the direction of the greatest decrease of the error margin MSE and in the direction of the negative gradient of the error margin MSE, respectively, wherein the parameter μ controls the step size. The known LMS algorithm for computing the filter coefficients $b_k[n]$ of an adaptive filter used in the further course in an exemplary manner, can be described as follows:

$$b_k[n+1]=b_k[n]=2\cdot\mu\cdot e[n]\cdot x[n-k] \text{ for } k=0, \ldots N-1.$$

The new filter coefficients $b_k[n+1]$ correspond to previous filter coefficients $b_k[n]$ plus a correction term, which is a function of the error signal e[n] and of the input signal vector x[n−k], which is assigned to the respective filter coefficient vector $b_k$. The LMS convergence parameter μ thereby represents a measure for the speed and for the stability of the adaptation of the filter.

It is also known that the adaptive filter, in the instant example a FIR filter, converges to a known and so-called Wiener filter in response to the use of the LMS algorithm, when the following condition applies for the amplification factor μ:

$$0<\mu<\mu_{max}=1/[(N+1)\cdot E\{x^2[n]\}]$$

whereby N represents the order of the FIR filter and $E\{x^2[n]\}$ represents the signal output of the reference signal x[n]. In practice, the used step size and the convergence parameter respectively, is often chosen to be $\mu=\mu_{max}/10$. The least mean square algorithm of the adaptive LMS filter may thus be realized as outlined below.

1. Initialization of the algorithm by setting the control variable to n=0; selecting the start coefficients $b_k[n=0]$ for k=0, . . . , N−1 at the onset of the execution of the algorithm (e.g., $b_k[0]=0$ for k=0 . . . N−1 and e[0]=d[0]); and selecting the amplification factor $\mu<\mu_{max}$, e.g., $\mu=\mu_{max}/10$.
2. Storing of the reference signal x[n] and of the signal d[n].
3. FIR filtering of the reference signal according to:

$$y[n]=\sum_{k=0}^{N} b_k[n]\cdot x[n-k]$$

4. Determination of the error: e[n]=d[n]−y[n]
5. Updating of the coefficients according to:

$$b_k[n+1]=b_k[n]+2\cdot\mu\cdot e[n]\cdot x[n-k] \text{ for } k=0, \ldots, N.$$

6. Execution of the next iteration step n=n+1 and repeating steps 2 to 6.

Figure 2:
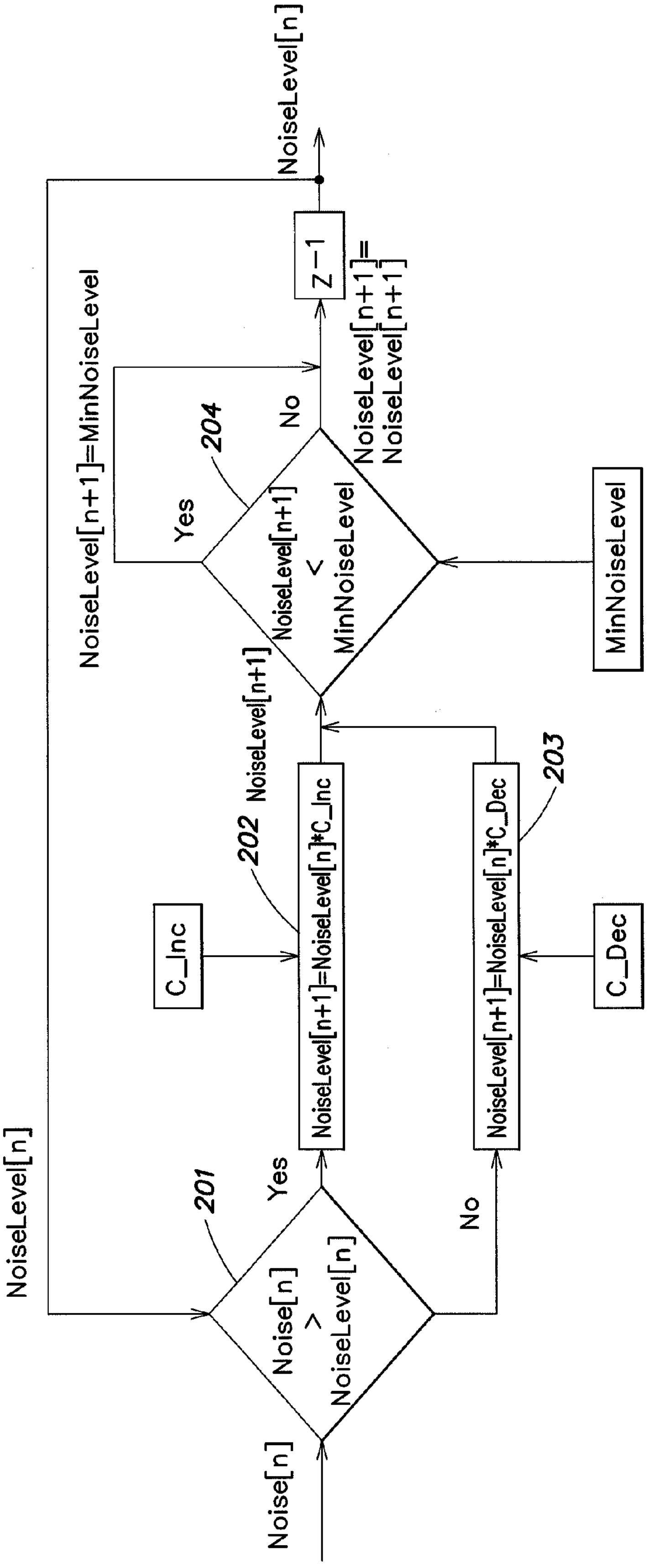
FIG. 2 is a signal flow chart illustration of a memory less smoothing filter.

FIG. 2 shows a signal diagram of a technique for estimation of the power spectral density of background noise using smoothing filtering, but not voice detection. FIG. 2 shows an initial comparator step 201 and a second comparator step 204 as well as an initial calculation step 202 for computing the increase in the estimation of the power spectral density and a second calculation step 203 for computing the drop in the estimation of the power spectral density.

A signal Noise[n], which may be the signal of a microphone measuring the background noise or the error signal of an adaptive filter (see FIG. 1), is compared in the comparator step 201 with the estimate NoiseLevel[n] of the estimated power spectral density computed in a previous step of the algorithm. If the current estimate value, Noise[n], is greater than the estimate NoiseLevel[n] of the estimated power spectral density computed in the previous step of the algorithm ("yes" path of step 201), a fixed predefined increment value C_Inc is added to the estimate NoiseLevel[n] computed in the previous step of the algorithm to produce a new, higher value NoiseLevel[n+1] for estimation of the power spectral density.

The increment value C_Inc is constant and its value is independent of the amount the current value Noise[n]. This approach prevents any voice signals that may exist in the current value Noise[n], which typically have faster rises in level than the broadband background noise in the interior of an automobile, from significantly affecting the algorithm and consequently the computation of the estimate value.

However, if the current value Noise[n] in the step 201 is smaller than the estimate NoiseLevel[n] of the estimated power spectral density computed in the previous step of the algorithm ("no" path in the step 1), a fixed predefined decrement value C_Dec is subtracted from the estimate NoiseLevel [n] computed in the previous step of the algorithm to produce a new, lower value NoiseLevel[n+1] for estimation of the power spectral density.

The decrement value C_Dec is constant and its value is independent of the amount the current value Noise[n]. This has the consequence that for both cases, i.e., for the increment or the decrement case, the estimated difference, in the rate of change of the level of the Noise[n] signal, is ignored. The newly computed estimate NoiseLevel[n+1] is compared in the step 204 with a fixed predefined minimum value MinNoiseLevel.

For the case that the newly computed estimate value NoiseLevel[n+1] is smaller than the fixed predefined minimum value MinNoiseLevel ("yes" path of step 204), the value of the newly computed estimate value NoiseLevel[n+1] is replaced by the value of the fixed predefined minimum value MinNoiseLevel; in other words, the estimate value is limited to the minimum value MinNoiseLevel. The purpose of this fixed predefined minimum value MinNoiseLevel is to prevent the NoiseLevel[n+1] signal from falling below this specified threshold value even if the Noise[n] signal is actually lower. In this way, the algorithm does not respond too slowly even for subsequent fast, strong rises in the Noise[n] signal.

Since the maximum possible rate of increasing the estimate value for the power spectral density is specified by the fixed predefined, constant value C_Inc of the increment, a much too large difference in value between the newly computed estimate value NoiseLevel[n+1] and the actual value Noise[n] can occur in the event of fast, strong rises in the value Noise [n] that significantly exceed the value C_Inc of the increment for each time unit of the algorithm computation cycle. As a consequence, the adjustment of the estimate value NoiseLevel[n+1] to the actual value Noise[n] of the power spectral density may experience delays that do not allow any meaningful evaluation and re-use of the computed estimate value. On the other hand, if the newly computed estimate value NoiseLevel[n+1] is greater than the fixed minimum value MinNoiseLevel ("no" path of step 204), the newly computed estimate value NoiseLevel[n+1] is retained and the algorithm begins with the computation of the next value in the estimate of the power spectral density.

The disadvantage of the method can be that both for the incrementing and decrementing of the estimate value of the power spectral density the rate of change in level of the Noise[n] signal cannot be sufficiently approximated by the estimate value if the change in level of the background noise, for example, rises over a lengthy period (i.e., over several computation cycles of the algorithm in the same direction) and the rise in level of the Noise[n] signal for each computation cycle is considerably larger than the fixed increment C_Inc, which defines the maximum rise in level of the estimate value of the power spectral density in any given calculation step. A similar problem occurs if the change in level of the background noise falls over a lengthy period (i.e., over several computation cycles of the algorithm in the same direction) and the rise in level of the Noise[n] signal for each computation cycle is considerably larger than the fixed decrement C_Dec, which defines the maximum decrement in level of the estimate value of the power spectral density in any given calculation step. At this point, the novel system and method increases the quality of the estimate of the power spectral density in this regard without increasing the susceptibility of the algorithm in response to concurrently arising voice signals In the design shown in FIG. 2, the algorithm is suitable only for estimating the overall level of the background noise throughout the entire frequency range that is observed. However, an appropriate frequency resolution of the estimated power spectral density is required for a suitable application of the estimate value of the power spectral density for noise suppression by filtering the signal. Thus, the illustrated algorithm has to be performed for each individual spectral line in the frequency range of interest (e.g. the frequency range of voice signals), which demands a high level of computing power of a digital signal processor.

Figure 3:
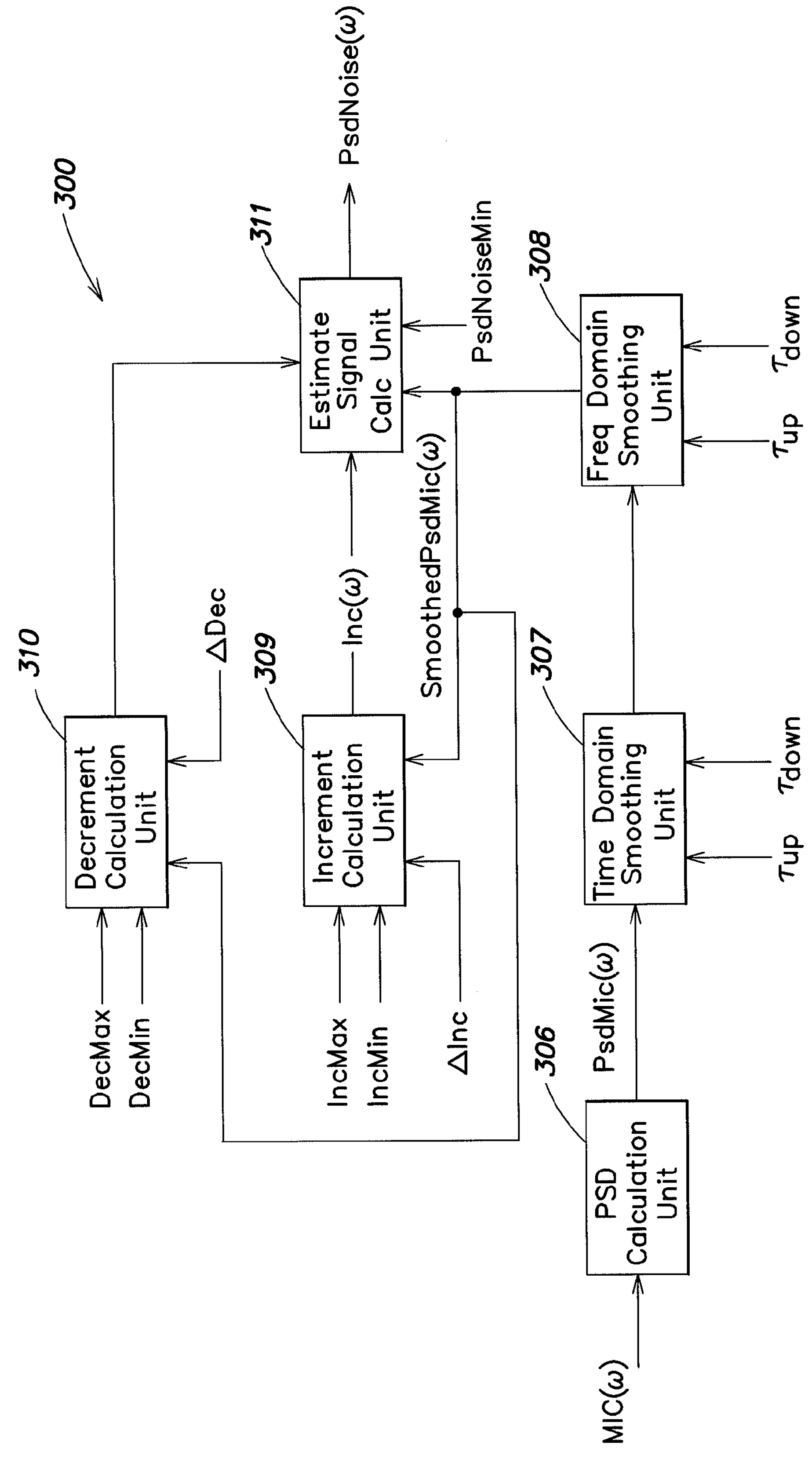
FIG. 3 is a block diagram illustration of a system for estimating the background noise.

FIG. 3 is a block diagram illustration of a system 300 that estimates the power spectral density of background noise without using voice detection. The system illustrated in FIG. 3 is, e.g., implemented using a digital signal processor. The system of FIG. 3 shows a power spectral density calculation unit 306, a time domain signal smoothing unit 307, a frequency domain signal smoothing unit 308, an increment calculation unit 309, a decrement calculation unit 310 and an estimate signal smoothing unit 311. The power spectral density calculation unit 306 computes the power spectral density (PSD) from an input signal MIC(ω), which yields the output signal PsdMic(ω) representing the power spectral density of the input signal MIC(ω). The input signal may be, e.g., a microphone signal as shown here, or an error signal of an adaptive filter (see FIG. 1). Then, as shown in FIG. 3, the signal PsdMic(ω) is smoothed in the time domain (smoothing over time) using the time domain signal smoothing unit 307.

The smoothing in the time domain has two different smoothing time constants, i.e. $\tau_{up}$ and $\tau_{Down}$. The first time constant $\tau_{up}$ is applied if the signal rises, i.e., if it has a positive gradient; in contrast the time constant $\tau_{Down}$ is applied if the signal decreases, i.e., if it has a negative gradient. Hence the application of the smoothing in the time domain is different to the smoothing in the frequency domain and thus both need not be mixed. In addition, the main purpose of different up and down smoothing time constant is to address the sensitivity of human ears to rising or falling noise as they tend to be more sensitive to rising noise levels as to falling noise levels, provided, that both happen to have the same time constant. Hence it is necessary to account for that fact by applying different time constants, one for the rising case and one for the decreasing case.

In an additional processing step of the system of FIG. 3, the output of the time domain signal smoothing unit 307 is smoothed in the frequency domain (smoothing over frequency) using the frequency domain signal smoothing unit 308. This smoothing is again conducted twice, once starting from a frequency $f=f_{min}$ up to a frequency $f=f_{max}$ and using a coefficient $\tau_{up}$, and once starting from a frequency $f=f_{max}$ to $f=f_{min}$, using a coefficient $\tau_{down}$. The upward and downward smoothing steps can be of any order and the frequency $f=f_{min}$ refers to the minimum frequency chosen for processing, while the frequency $f=f_{max}$ refers to the maximum frequency chosen for processing. The frequencies $f_{min}$ and $f_{max}$ may be chosen such that a frequency range is included which covers the relevant frequency range of the acoustic perception in the human ear. The coefficients $\tau_{up}$ and $\tau_{down}$ for the smoothing of the PsdMic(ω) signal over frequency are selected in such a way that the greatest possible reduction in spectral fluctuations of the PsdMic(ω) signal is achieved to reduce the required computing power for the subsequent steps in the present method. At the same time this selection is made in a way that the necessary spectral information is retained so as to derive the frequency-dependent properties of the PsdMic(ω) signal relevant for perception by the human ear. The psychoacoustic evaluation steps (and units) to be considered here are shown further below.

Usually, $\tau_{up}$ and $\tau_{Down}$ are chosen as equal values due to the fact that the main purpose of the up and down smoothing is to avoid frequency bias, which would occur if one would smooth in only one frequency direction. Hence, if one would smooth in the upward frequency direction with a different smoothing time constant as for the smoothing in the downward direction again a certain kind of frequency shift (bias) is created which originally was intended to be avoided by applying the up and down smoothing.

The signal SmoothedPsdMic(ω) is obtained from the PsdMic(ω) signal through the smoothing in the time domain (smoothing over time, time domain signal smoothing unit 307) and in the frequency domain (smoothing over frequency, frequency domain signal smoothing unit 308). The SmoothedPsdMic(ω) signal is used as an input signal for the subsequent processing steps conducted in the increment calculation unit 309, the decrement calculation unit 310, and the estimate signal smoothing unit 311 in order to estimate the power spectral density of background noise without the use of a voice detection mechanism.

The increment calculation unit 309 designates a calculation step for computing the relevant increments Inc(ω) for estimation of the power spectral density in the case of level rises in the SmoothedPsdMic(ω) signal for all spectral components of the smoothed signal SmoothedPsdMic(ω) to be considered. The decrement calculation unit 310 computes the relevant decrements Dec(ω) for estimation of the power spectral density in the case of decreasing levels in the SmoothedPsdMic(ω) signal for all spectral components of the smoothed signal SmoothedPsdMic(ω) to be considered. The estimate signal smoothing unit 311 refers to a smoothing filtering as shown in FIG. 2, for which the increments and decrements for estimation of the rise or fall in level of the power spectral density are not specified as constants, but are adaptively dependent on the rate of rise or fall in the level.

Using the increments Inc(ω) computed in the increment calculation unit 309, a current estimate value PsdNoise(ω) of the power spectral density is computed under consideration of a fixed minimum threshold PsdNoiseMin for each relevant spectral component of the smoothed signal SmoothedPsdMic (ω). The fixed minimum threshold PsdNoiseMin corresponds to the minimum value of the estimate value of the power spectral density shown in FIG. 2 as MinNoiseLevel.

As described further above, the disadvantage of known techniques in the field is, for both incrementing and decrementing of the estimate value of the power spectral density, that the rate of change of level of the background noise cannot be adequately approximated by the estimate value in all cases. For example, this is the case if the change in level of the background noise rises over a lengthy period (i.e., over several computation cycles of the algorithm) and the rise in level of the background noise for each computation cycle of the algorithm is larger than the fixed increment, which defines the maximum rise in level of the estimate value of the power spectral density. Likewise a similar problem exists if the level of the background noise decreases over a lengthy period (i.e., over several computation cycles of the algorithm) and the decrease in level of the background noise for each computation cycle of the algorithm is larger than the fixed decrement, which defines the maximum decrement in level of the estimate value of the power spectral density.

The system of FIG. 3 for estimating the rise in level of the power spectral density in the case of rises in level of the background noise using an increment calculation unit 309 as shown in FIG. 3 eliminates this disadvantage without incurring a large, unwanted dependency on a voice signal present at the same time. Use is made of the fact that in particular the timing behavior differs considerably between voice signals and background noise. While voice signals typically exhibit fast increases and decreases in level over time (speech dynamics), this is not generally the case for typical background noise signals, such as experienced in the interior of automobiles. Nevertheless, the known techniques do not respond in particular cases fast enough to the changes in level of background noise typical for surrounding conditions, such as in automobiles.

This applies as described specially for strong rises in level in background noise that occur continuously over a lengthy period, e.g., over a period of about 2 to 3 seconds. A continuous rise in level over such a period differs significantly from the rises in level expected in voice signals, in which continuous rises in level do not occur for as long as about 2 to 3 seconds, a lengthy period for speech dynamics. This clear-cut distinction in the dynamics of the observed signals is utilized as described below to increase the speed of response of the present system and method. Fast, strong increases and decreases in the level of background noise are accounted for superior to known techniques without increasing the susceptibility of the algorithm to concurrent speech signals.

In the following, the increment calculation unit 309 (FIG. 3) which computes the increments of the estimate value of the power spectral density in response to rises in level of the background noise is illustrated in greater detail. Starting from a specified minimum value of the increment IncMin, for example, 0.5 dB per second, the new value of the increment Inc(ω) used in the computation of the estimate value is increased by a fixed value ΔInc (for example, 0.01 dB per frame, e.g., with a frame length e.g., of 512 samples at a sampling frequency of 44100 Hz) for cases in which the newly computed signal SmoothedPsdMic(ω) of the signal smoothed in the time and frequency domains by the time domain signal smoothing unit 307 and the frequency domain signal smoothing unit 308 (SmoothedPsdMic(ω)) is larger than the estimate value PsdNoise(ω) of the power spectral density computed in the previous computation cycle. A computation cycle may have, for example, a duration of 10 ms. In this way, the value of the increment Inc(ω) is continuously increased each time by 0.01 dB for each computation cycle of the algorithm in cases in which the value of the smoothed signal SmoothedPsdMic(ω) is continuously larger than the estimate value PsdNoise(ω) of the power spectral density computed in the previous computation cycle.

It can therefore be seen that the increment Inc(ω) for a rise in level of the smoothed signal SmoothedPsdMic(ω) lasting one second, starting from a minimum value IncMin of 0.5 dB, is eventually increased to 1.5 dB because Inc(ω) after one second, i.e., 100 computation cycles, each 10 ms long, is calculated as follows:

$$Inc\ (\omega)=Inc\ Min+100*\Delta Inc$$

If the value of the smoothed signal SmoothedPsdMic(ω) obtained as the result of a new computation cycle is smaller than the estimate value PsdNoise(ω) of the power spectral density computed in the previous computation cycle, the value of the increment Inc(ω) is reset to the specified minimum value IncMin and the algorithm changes to the computation mode for determining the decrements for estimating the power spectral density for falling levels. The maximum possible value for the increment Inc(ω) is defined by the fixed predefined value IncMax, for example, 2.5 dB. Thus, the maximum value IncMax of the increment Inc(ω) cannot be achieved before at least a 2.5 second period of continuous rising in the level of the smoothed signal SmoothedPsdMic (ω) elapses, wherein during this timeframe the value of the smoothed signal SmoothedPsdMic(ω) has to be greater than the estimate value PsdNoise(ω) of the power spectral density of the background noise computed in the previous computation cycle.

It is evident that with an equivalent algorithm the values of the decrement Dec(ω) for estimation of the value PsdNoise (ω) of the power spectral density of the background noise can also be computed for a decline in the level of the smoothed signal SmoothedPsdMic(ω). The estimate value PsdNoise(ω) of the power spectral density of the background noise is always reduced by the decrement Dec(ω) if the value of the smoothed signal SmoothedPsdMic(ω) is smaller than the estimate value PsdNoise(ω) of the power spectral density of the background noise computed in the previous computation cycle. Corresponding to the illustration of the increment calculation unit 309 for the actual increment, a decrement calculation unit 310 is employed in this case. Here, a specified value DecMin for the minimum value of the computed decrement Dec(ω), a specified value DecMax for the maximum value of the computed decrement Dec(ω) and a specified value ΔDec for adaptive adjustment of the decrement Dec(ω) is used.

Starting again from a specified minimum value of the decrement DecMin, for example, 1 dB per second, the new value of the decrement Dec(ω) used in the computation of the estimate value is increased by a fixed value ΔDec (for example, 0.05 dB per frame e.g., with a frame length e.g., of 512 samples at a sampling frequency of 44.1 kHz) for cases in which the newly computed signal SmoothedPsdMic(ω) of the signal smoothed in the time and frequency domains by the time domain signal smoothing unit 307 and the frequency domain signal smoothing unit 308 (SmoothedPsdMic(ω)) is smaller than the estimate value PsdNoise(ω) of the power spectral density computed in the previous computation cycle. In this way, the value of the decrement Dec(ω) is increased by 0.05 dB for each computation cycle of the algorithm in cases in which the value of the smoothed signal SmoothedPsdMic (ω) is smaller than the estimate value PsdNoise(ω) of the power spectral density computed in the previous computation cycle. It can therefore be seen from the exemplary values that the decrement Dec(ω) for a decline in level of the smoothed signal SmoothedPsdMic(ω) lasting one second, starting from a minimum value DecMin of 1 dB, is increased to 6 dB because Dec(ω) after one second, i.e., 100 computation cycles, each 10 ms long, is calculated as follows:

$$Dec(\omega)=DecMin+100*\Delta Dec$$

If the value of the smoothed signal SmoothedPsdMic(ω) obtained as the result of a new computation cycle is larger than the estimate value PsdNoise(ω) of the power spectral density computed in the previous computation cycle, the value of the decrement Dec(ω) is reset to the specified minimum value DecMin and the algorithm changes to the computation mode to determine the increments for estimating the power spectral density for rising levels. The maximum possible value for the decrement Dec(ω) is likewise defined by the fixed predefined value DecMax, for example, 11 dB. Thus for the example given, the maximum value DecMax of the decrement Dec(ω) cannot be achieved before at least a two-second period of continuous decline in the level of the smoothed signal SmoothedPsdMic(ω) elapses, where the value of the smoothed signal SmoothedPsdMic(ω) has to be smaller than the estimate value PsdNoise(ω) of the power spectral density of the background noise computed in the previous computation cycle.

As described further above, continuous increases and decreases in level over this period of seconds differ considerably from the increases and decreases in the level of voice signals which occur in much shorter intervals, for which the described algorithm shows itself to be insensitive to unwanted effects of voice signals occurring at the same time as the background noise to be estimated. Thus the estimate computation result is not corrupted. The algorithm described above can again be performed for all spectral components of the signal SmoothedPsdMic(ω) with individual values for the quantities ΔInc, ΔDec, IncMin, DecMin, IncMax and DecMax for each spectral component. The values for ΔInc, ΔDec, IncMin, DecMin, IncMax, DecMax and the duration of the individual computation cycles represent examples to illustrate an exemplary system and method, and can have other values depending on the application and ambient conditions, although the basic function of the underlying algorithm is retained.

The coefficients $\tau_{up}$ and $\tau_{down}$ mentioned earlier for smoothing over time and $\tau_{up}$ and $\tau_{down}$ for smoothing over frequency of the signal PsdMic(ω) can be determined, e.g., empirically from simulations and sample test circuits under different ambient conditions. The smoothing of the PsdMic (ω) signal in the frequency domain (smoothing over frequency) may be carried out twice with the calculated coefficients $\tau_{up}$ and $\tau_{down}$, once in the direction from low to high frequencies, and once in the direction from high to low frequencies, whereby frequency shifts (bias) is avoided in the frequency representation of the signal.

Alternatively, the coefficients $\tau_{up}$ and $\tau_{down}$ for smoothing over time and $\tau_{up}$ and $\tau_{down}$ for smoothing over frequency may be derived from the known psychoacoustic properties of the human ear to reduce the informational content of the smoothed signal SmoothedPsdMic(ω), i.e., the data rate. This is favorable to the extent that major benefits are obtained with regard to the smaller amount of computing power needed for the digital signal processor employed. Advantages can arise from a lesser dynamic level fluctuation of the smoothed signal SmoothedPsdMic(ω) in the time domain and a reduced number of spectral components in the frequency domain of the SmoothedPsdMic(ω) signal to be individually considered.

To achieve the optimum positive effects, physical quantities cannot be used exclusively; rather psychoacoustic properties of the human ear have to be considered. Psychoacoustics is a subset of psychophysics that regards the aural impressions that occur whenever a sound wave reaches the human ear. Based on human aural impressions, frequency group formation in the inner ear, signal processing in the human inner ear, and simultaneous and temporary masking effects in the time and frequency domains, a model can be created that indicates what acoustic signals or combinations of acoustic signals can be perceived or not perceived by a human with undamaged hearing in the presence of noise signals, such as background noise.

The threshold at which a test tone can just be perceived in the presence of a noisy signal (also known as a masker) is referred to as the masked threshold. In contrast, the minimum audible threshold refers to the value at which a test tone can just be perceived in a quiet environment, where the area between the minimum audible threshold and a masked threshold caused by a masker, such as background noise, is known as the masking area.

Since noise signals, for example, the background noise in an automobile, are subject to dynamic changes both with regard to their spectral composition as well as their temporal behavior, a psychoacoustic model considers the dependencies of the masking on the audio signal level, the spectral composition and the temporal characteristics. The basis for the modeling of the psychoacoustic masking is given by fundamental characteristics of the human ear, particularly the inner ear. The inner ear is located in the so-called petruous bone and filled with incompressible lymphatic fluid.

The inner ear is shaped like a spiral (cochlea) with approximately 2½ turns. The cochlea in turn comprises parallel canals, the upper and lower canals separated by the basilar membrane. The organ of Corti rests on the membrane and contains the sensory cells of the human ear. If the basilar membrane is made to vibrate by sound waves, nerve impulses are generated, i.e., no nodes or antinodes arise. This results in an effect that is crucial to hearing, the so-called frequency/location transformation on the basilar membrane, with which psychoacoustic masking effects and the refined frequency selectivity of the human ear can be explained.

The human ear groups different sound waves that occur in limited frequency bands together so that they are processed as a single acoustic event. These frequency bands are known as critical frequency groups or as critical bandwidth (CB). The basis of the CB is that the human ear compiles sounds in particular frequency bands as a common audible impression in regard to the psychoacoustic hearing impressions arising from the sound waves. Sonic activities that occur within a frequency group affect each other differently than sound waves occurring in different frequency groups. Two tones with the same level within one frequency group, for example, are perceived as being quieter than if they were in different frequency groups.

As a test tone is then audible within a masker when the energies are identical and the masker is in the frequency band whose center frequency is the frequency of the test tone, the sought bandwidth of the frequency groups can be determined. In the case of low frequencies, the frequency groups have a bandwidth of 100 Hz. For frequencies above 500 Hz, the frequency groups have a bandwidth of about 20% of the center frequency of the corresponding frequency group.

If all critical frequency groups are placed side-by-side throughout the entire audible range, a hearing-oriented non-linear frequency scale is obtained, which is known as tonality and which has the unit "bark". It represents a distorted scaling of the frequency axis so that frequency groups have the same width of exactly one bark at every position. The non-linear relationship between frequency and tonality is rooted in the frequency/location transformation on the basilar membrane. The tonality function was defined in tabular and equation form by Zwicker (see Zwicker, E.; Fastl, H.; Psychoacoustics—Facts and Models, 2nd edition, Springer-Verlag, Berlin/Heidelberg/New York, 1999) on the basis of masked threshold and loudness examinations. It can be seen that in the audible frequency range from 0 to 16 kHz frequency groups can be placed in series so that the associated tonality range is from 0 to 24 barks. The tonality z in barks is calculated as follows:

$$z/bark = 13*\arctan\left(0.76\frac{f}{\text{kHz}}\right) + 3.5*\arctan\left(\frac{f}{7.5\text{kHz}}\right)^2$$

and the corresponding frequency group width $\Delta f_G$ as:

$$\Delta f_G/\text{Hz} = 25 + 75*\left[1 + 1.4*\left(\frac{f}{\text{kHz}}\right)^2\right]^{0.69}$$

Moreover, the terms loudness and sound intensity refer to the same quantity of impression and differ only in their units. They consider the frequency-dependent perception of the human ear. The psychoacoustic dimension "loudness" indicates how loud a sound with a specific level, a specific spectral composition and a specific duration is subjectively perceived. The loudness becomes twice as large if a sound is perceived to be twice as loud, which allows different sound waves to be compared with each other in reference to the perceived loudness. The unit for evaluating and measuring loudness is a sone. One sone is defined as the perceived loudness of a tone having a loudness level of 40 phons, i.e., the perceived loudness of a tone that is perceived to have the same loudness as a sinus tone at a frequency of 1 kHz with a sound pressure level of 40 dB.

In the case of medium-sized and high intensity values, an increase in intensity by 10 phons causes a two-fold increase in loudness. For low sound intensity, a slight rise in intensity causes the perceived loudness to be twice as large. The loudness perceived by humans depends on the sound pressure level, the frequency spectrum and the timing characteristics of the sound, and is also used for modeling masking effects. For example, there are also standardized measurement practices for measuring loudness according to DIN 45631 and ISO 532 B.

Figure 4:
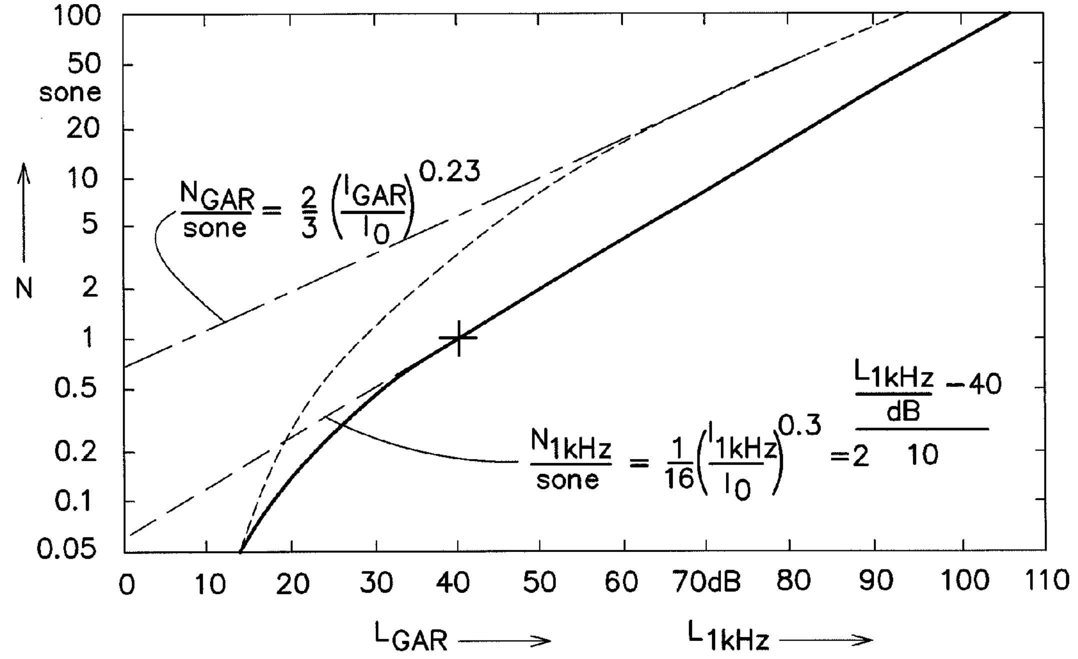
FIG. 4 is a graph illustrating the loudness as a function of the level of a sinusoidal signal and a broadband noise signal.

FIG. 4 shows an example of the loudness $N_{1kHz}$ of a stationary sinus tone with a frequency of 1 kHz and the loudness $N_{GAR}$ of a stationary uniform excitation noise in relation to the sound level, i.e., for signals for which time effects have no influence on the perceived loudness. Uniform excitation noise (GAR) is defined as a noise that has the same sound intensity in each frequency group and therefore the same excitation. FIG. 4 shows the loudness in sones in logarithmic scale versus sound pressure levels. For low sound pressure levels, i.e., when approaching the minimum audible threshold, the perceived loudness N of the tone falls dramatically.

A relationship exists between loudness N and sound pressure level for high sound pressure levels, this relationship is defined by the equations shown in the figure. "I" refers to the sound intensity of the emitted tone in watts per $m^2$, where $I_0$ refers to the reference sound intensity of $10^{-12}$ watts per $m^2$, which corresponds at medium frequencies to roughly the minimum audible threshold (see below). It becomes clear that the loudness N is a useful for determining masking by complex noise signals, and is thus a necessary requirement for a model of psychoacoustic masking through spectrally complex, time-dependent sounds.

If the sound pressure level is measured, which is needed to just about perceive a tone as a function of the frequency, the so-called minimum audible threshold is obtained. Acoustic signals whose sound pressure levels are below the minimum audible threshold cannot be perceived by the human ear, even without the simultaneous presence of a noise signal.

In contrast, the so-called masked threshold is defined as the threshold of perception for a test sound in the presence of a noisy signal. If the test sound is below this psychoacoustic threshold, the test sound is fully masked. This means that all information within the psychoacoustic range of the masking cannot be perceived. Known compression and data reduction algorithms for audio signals also use this audio signal masking property, for example, to reduce information components in the signal under test without causing a perceivable deterioration in the quality of the actual signal. A known method is the ISO-MPEG audio compression process for layers 1, 2 and 3 devised by the Fraunhofer Institute for Integrated Circuits.

Numerous trials have demonstrated that masking effects can be measured for all kinds of human hearing. Unlike many other psychoacoustic impressions, differences between individuals are rare and can be ignored, meaning that a general psychoacoustic model of masking by sound can be produced. The psychoacoustic aspects of the masking are utilized in the case shown herein to smooth the measured power spectral density in real time in compliance with the audio characteristics in such a way that components of the measured power spectral density psychoacoustically masked in the time and frequency domains are not included in the processing for subsequent estimation of the power spectral density. As a consequence, an initial significant reduction in the subsequent processing by the present algorithm is obtained in regard to the number of spectral components to be handled since individual components of the power spectral density, provided they are masked by other components, are not perceivable and therefore do not need to be considered.

A distinction is made between two major types of masking, which result in different characteristics of masked thresholds. These types are the simultaneous masking in the frequency domain and masking in the time domain by effects of the masker along the time axis. Mixes of these two masking types also occur in signals such as ambient noises or music.

Simultaneous masking means that a masking sound and useful signal occur at the same time. If the shape, bandwidth, amplitude and/or frequency of the masker changes in such a way that the frequently sinus-shaped test signals are just audible, the masked threshold can be determined for simultaneous masking throughout the entire bandwidth of the audible range, i.e., mainly for frequencies between 20 Hz and 20 kHz.

Figure 5:
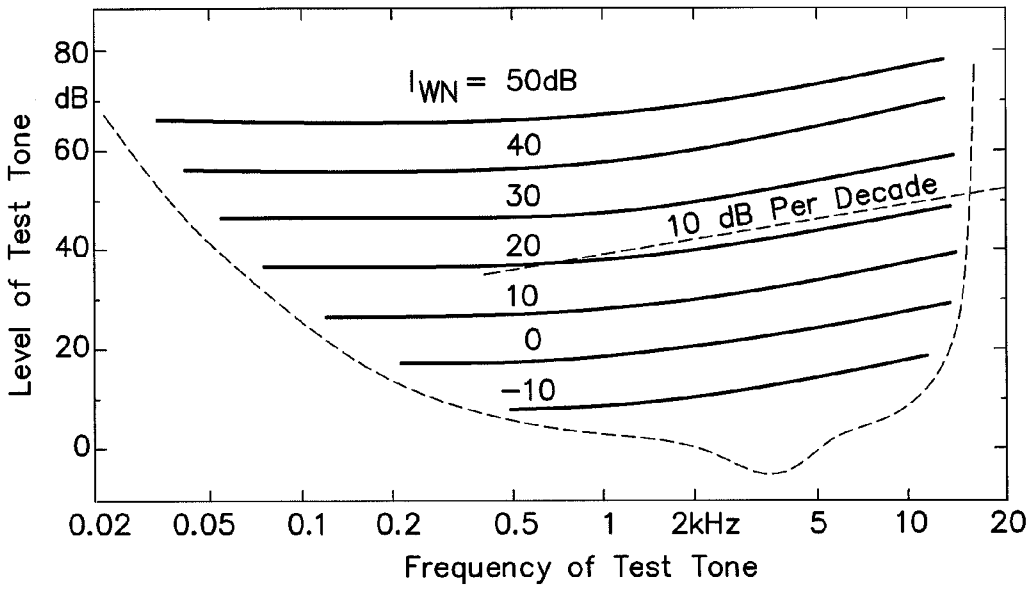
FIG. 5 is a graph illustrating masking through white noise.

FIG. 5 shows the masking of a sinusoidal test tone by white noise. The sound intensity of a test tone just masked by white noise with the sound intensity IWN is displayed in relation to its frequency. In FIG. 5, the minimum audible threshold is displayed as a dotted line. The minimum audible threshold of a sinus tone for masking by white noise is obtained as follows: below 500 Hz, the minimum audible threshold of the sinus tone is about 17 dB above the sound intensity of the white noise. Above 500 Hz the minimum audible threshold increases with about 10 dB per decade or about 3 dB per octave, corresponding to doubling the frequency.

The frequency dependency of the minimum audible threshold is derived from the different critical bandwidth (CB) of the human ear at different center frequencies. Since the sound intensity occurring in a frequency group is compiled in the perceived audio impression, a greater overall intensity is obtained in wider frequency groups at high frequencies for white noise whose level is independent of frequency. The loudness of the sound also rises correspondingly (i.e., the perceived loudness) and causes increased masked thresholds. This means that the purely physical dimensions (such as sound pressure levels of a masker, for example) are inadequate for the modeling of the psychoacoustic effects of the masking, i.e., for deriving the masked threshold from test dimensions, such as sound pressure level and intensity. Instead, psychoacoustic dimensions such as loudness N are used in the present case. The spectral distribution and the timing characteristics of masking sounds play a major role, which is evident from the following figures.

If the masked threshold is determined for narrowband maskers, such as sinus tones, narrowband noise or critical bandwidth noise, it is shown that the resulting spectral masked threshold is higher than the minimum audible threshold, even in areas in which the masker itself has no spectral components. Critical bandwidth noise is used in this case as narrowband noise, whose level is designated as $L_{CB}$. FIG. 5 shows the masked thresholds of sinus tones measured as maskers due to critical bandwidth noise with a center frequency $f_c$ of 1 kHz, as well as of different sound pressure levels in relation to the frequency $f_T$ of the test tone with the level $L_T$. The minimum audible threshold is shown by the dashed line in FIG. 5.

Figure 6:
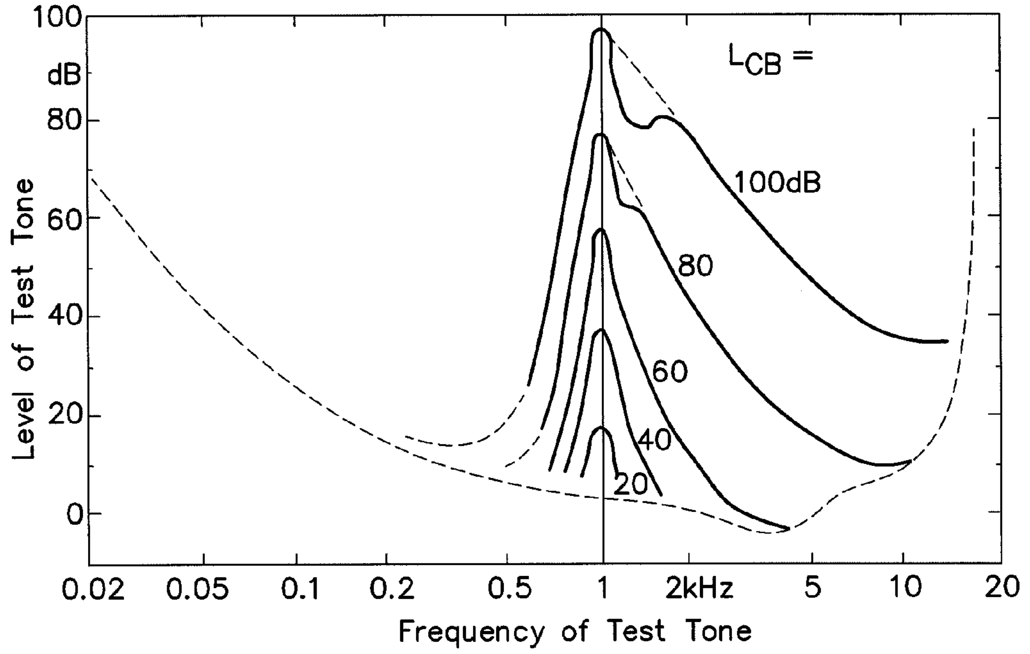
FIG. 6 is a graph illustrating masking in the frequency domain.

In the example of FIG. 6, the peaks of the masked thresholds rise by 20 dB if the level of the masker also rises by 20 dB. The relationship is therefore linearly dependent on the level $L_{CB}$ of the masking critical bandwidth noise. The lower edge of the measured masked threshold, i.e., the masking in the direction of low frequencies lower than the center frequency $f_e$, has a gradient of about −100 dB/octave that is independent of the level $L_{CB}$ of the masked thresholds. This large gradient is only reached on the upper edge of the masked threshold for levels $L_{CB}$ of the masker that are lower than 40 dB. With increases in the level $L_{CB}$ of the masker, the upper edge of the masked threshold becomes flatter and flatter, and the gradient is about −25 dB/octave for an $L_{CB}$ of 100 dB. This means that the masking in the direction of higher frequencies compared to the center frequency $f_c$ of the masker extends far beyond the frequency range in which the masking sound is present. Hearing responds similarly for center frequencies other than 1 kHz for narrowband, critical bandwidth noise. The gradients of the upper and lower edges of the masked thresholds are practically independent of the center frequency of the masker, as seen in FIG. 7.

Figure 7:
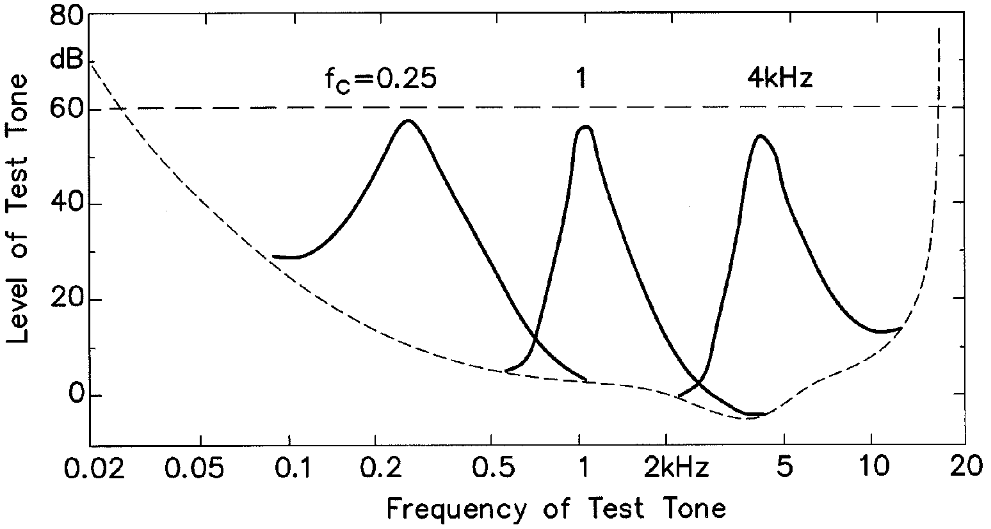
FIG. 7 is a graph illustrating the masked thresholds for frequency group-wide narrowband noise in the mid-frequencies 250 Hz, 1 kHz and 4 kHz.

FIG. 7 shows the masked thresholds for maskers from critical bandwidth noise in the narrowband with a level $L_{CB}$ of 60 dB and three different center frequencies of 250 Hz, 1 kHz and 4 kHz. The apparently flatter flow of the gradient for the lower edge for the masker with the center frequency of 250 Hz is due to the minimum audible threshold, which applies at this low frequency even at higher levels. Effects such as those shown are likewise included in the implementation of a psychoacoustic model for the masking The minimum audible threshold is again displayed in FIG. 7 by a dashed line.

Figure 8:
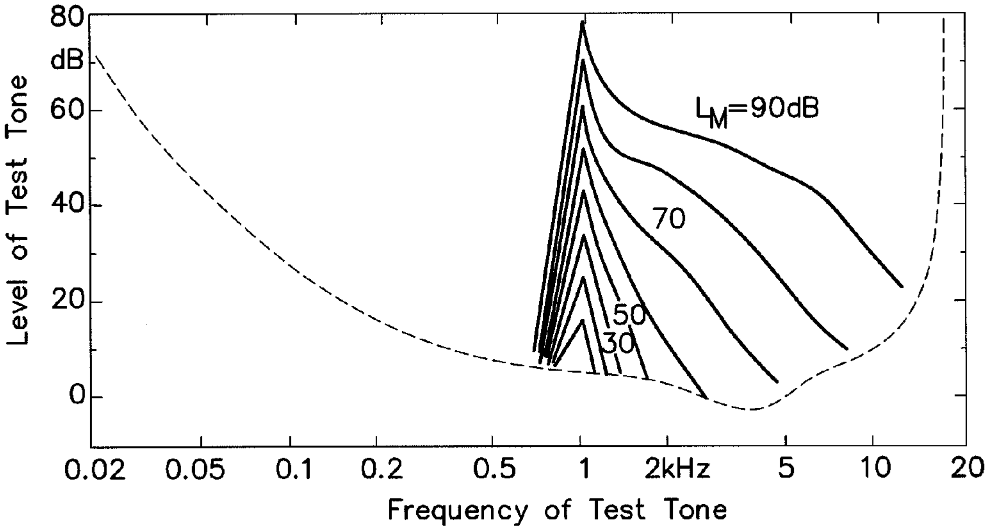
FIG. 8 is a graph illustrating the masking by sinus audio signals.

If the sinus-shaped test tone is masked by another sinus tone with a frequency of 1 kHz, masked thresholds are obtained in relation to the frequency of the test tone and level of the masker $L_M$ as shown in FIG. 8. As described earlier, the fanning-out of the upper edge in relation to the level of the masker can be clearly seen, while the lower edge of the masked threshold is practically independent of frequency and level. The upper gradient is measured to be about −100 to −25 dB/octave in relation to the level of the masker, and about −100 dB/octave for the lower gradient. A difference of about 12 dB exists between the level $L_M$ of the masking tone and the maximum values of the masked thresholds $L_r$.

This difference is significantly greater than the value obtained with critical bandwidth noise as the masker. This is because the intensities of the two sinus tones of the masker and of the test tone are added together at the same frequency, unlike the use of noise and a sinus tone as the test tone. Consequently, the tone is perceived much earlier, i.e., for low levels for the test tone. Moreover, when emitting two sinus tones at the same time, other effects (such as beats) arise, which likewise lead to increased perception or reduced masking.

The described simultaneous masking in the frequency domain has the effect that when smoothing in the frequency domain signal smoothing unit 308 (FIG. 3) only the spectral components of the PsdMic(ω) signal that are not masked by the critical bandwidth noise have to be considered. The algorithm can also be reduced for incrementing or decrementing the estimate value PsdNoise(ω) to the relevant spectral components and the masking characteristics caused and known by the components: a very significant reduction in the number of individual spectral components to be processed is therefore obtained if individual values for ΔInc, ΔDec, IncMin, DecMin, IncMax and DecMax are used.

Figure 9:
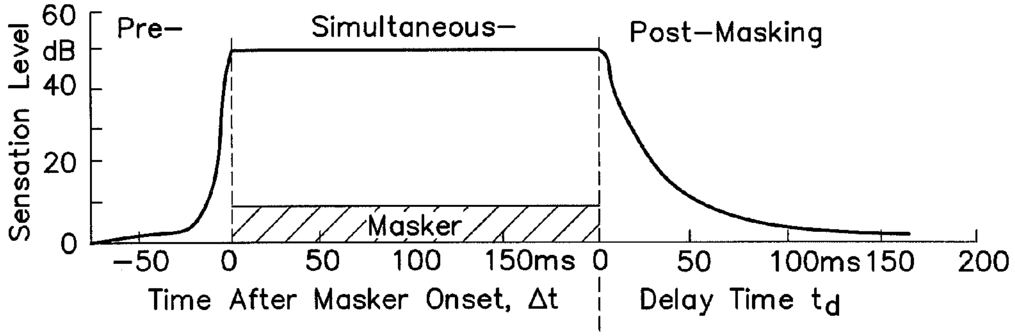
FIG. 9 is a representation of simultaneous, pre- and post-masking.

Along with the described simultaneous masking, another psychoacoustic effect of the masking is known, the so-called time masking Two different kinds of time masking are distinguished: pre-masking refers to the situation in which masking effects occur already before the abrupt rise in the level of a masker. Post-masking describes the effect that occurs when the masked threshold does not immediately drop to the minimum audible threshold in the period after the fast fall in the level of a masker. FIG. 9 schematically shows both the pre- and post-masking, which are explained in greater detail further below in connection with the masking effect of tone impulses.

To determine the effects of the time pre- and post-masking, test tone impulses of a short duration must be used to obtain the corresponding time resolution of the masking effects. Here the minimum audible threshold and masked threshold are both dependent on the duration of a test tone. Two different effects are known in this regard. These refer to the dependency of the loudness impression on the duration of a test impulse (see FIG. 10) and the relationship between the repetition rate of short tone impulses and loudness impression (see FIG. 11).

It is known that the sound pressure level of a 20-ms impulse has to be increased by 10 dB in comparison to the sound pressure level of a 200-ms impulse in order to obtain the identical loudness impression. Upward of an impulse duration of 200 ms, the loudness of a tone impulse is independent of its duration. It is known for the human ear that processes with a duration of more than about 200 ms represent stationary processes. Psychoacoustically certifiable effects of the timing properties of sounds exist if the sounds are shorter than about 200 ms.

Figure 10:
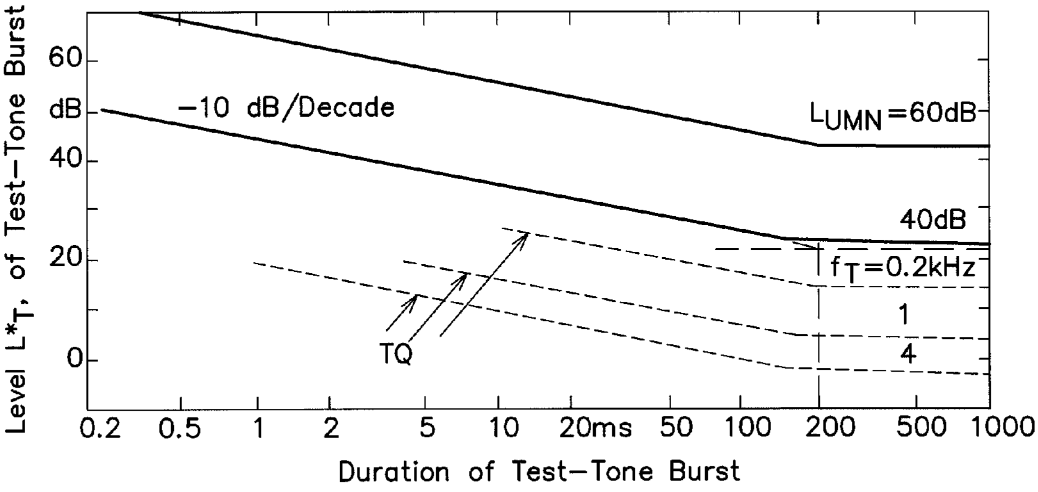
FIG. 10 is a graph illustrating the relationship between the loudness impression and the duration of a test tone impulse.

FIG. 10 shows the dependency of the perception of a test tone impulse on its duration. The dotted lines denote the minimum audible thresholds TQ of test tone impulses for the frequencies $f_T$=200 Hz, 1 kHz and 4 kHz in relation to their duration, whereby the minimum audible thresholds rise with about 10 dB per decade for durations of the test tone of less than 200 ms. This behavior is independent of the frequency of the test tone, the absolute location of the lines for different frequencies $f_T$ of the test tone reflects the different minimum audible thresholds at these different frequencies.

The continuous lines represent the masked thresholds for masking a test tone by uniform masking noise (UMN) with a level LUMN of 40 dB and 60 dB. Uniform masking noise is defined to be such that it has a constant masked threshold throughout the entire audible range, i.e., for frequency groups from 0 to 24 barks. In other words, the displayed characteristics of the masked thresholds are independent of the frequency $f_T$ of the test tone. Just like the minimum audible thresholds TQ, the masked thresholds also rise with about 10 dB per decade for durations of the test tone of less than 200 ms.

Figure 11:
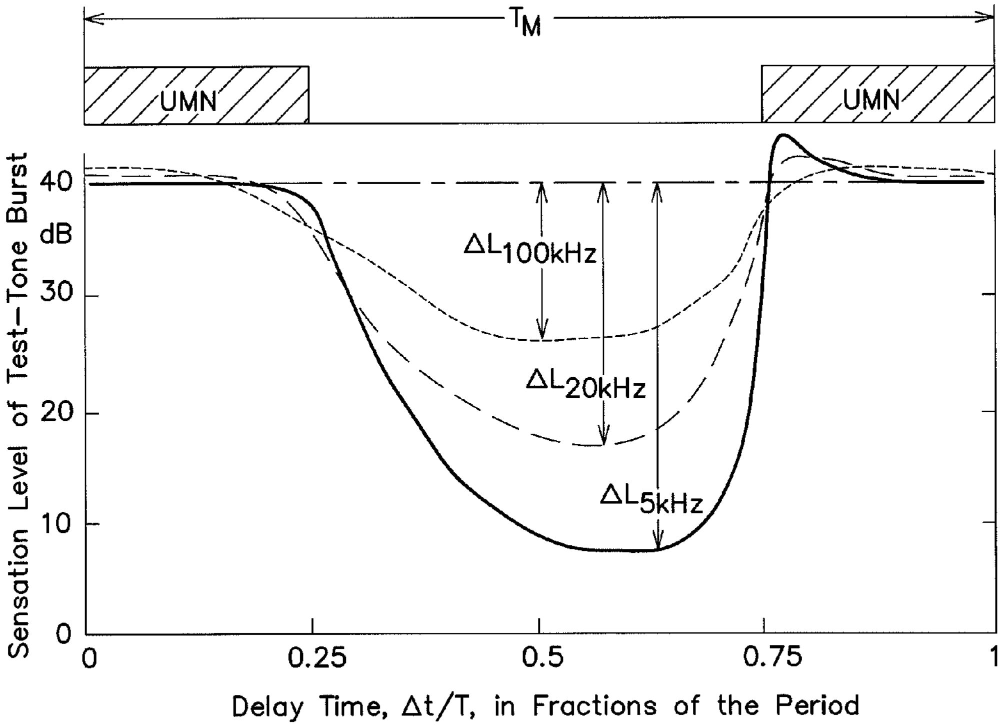
FIG. 11 is a graph illustrating the relationship between the masked threshold value and the repetition rate of a test tone impulse.

FIG. 11 shows the dependency of the masked threshold on the repetition rate of a test tone impulse with the frequency 3 kHz and a duration of 3 ms. Uniform masking noise is again the masker: it is modulated with a rectangular shape, i.e., it is switched on and off periodically. The examined modulation frequencies of the uniform masking noise are 5 Hz, 20 Hz and 100 Hz. The test tone is emitted with a subsequent frequency identical to the modulation frequency of the uniform masking noise. During the trial, the timing of the test tone impulses is correspondingly varied in order to obtain the time-related masked thresholds of the modulated noise.

FIG. 11 shows the shift in time of the test tone impulse along the abscissa standardized to the period duration $T_M$ of the masker. The ordinate shows the level of the test tone impulse at the calculated masked threshold. The dashed line represents the masked threshold of the test tone impulse for an non modulated masker (i.e., continuously present masker with otherwise identical properties) as reference points.

The flatter gradient of the post-masking in FIG. 11 in comparison to the gradient of the pre-masking is clear to see. After activating the rectangular-shaped modulated masker, the masked threshold is exceeded for a short period. This effect is known as an overshoot. The maximum drop ΔL in the level of the masked threshold for modulated uniform masking noise in the pauses of the masker is reduced as expected in comparison to the masked threshold for stationary uniform masking noise in response to an increase in the modulation frequency of the uniform masking noise, in other words, the masked threshold of the test tone impulse can fall less and less during its lifetime to the minimum value specified by the minimum audible threshold.

FIG. 11 also illustrates that a masker already masks the test tone impulse before the masker is switched on at all. This effect is known, as already mentioned earlier, as pre-masking, and is based on the fact that loud tones and noises (i.e., with a high sound pressure level) can be processed more quickly by the hearing sense than quiet tones. The pre-masking effect is considerably less dominant than that of post-masking. After disconnecting the masker, the audible threshold does not fall immediately to the minimum audible threshold, but rather reaches it after about 200 ms. The effect can be explained by the slow settling of the transient wave on the basilar membrane of the inner ear.

On top of this, the bandwidth of a masker also has direct influence on the duration of the post-masking. It is known that the particular components of a masker associated with each individual frequency group cause post-masking as shown in FIGS. 11 and 12.

Figure 12:
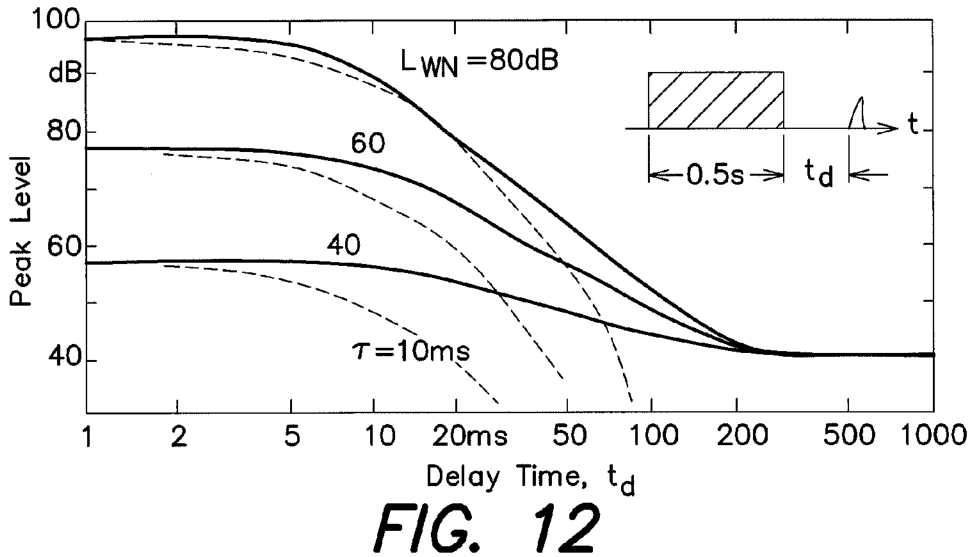
FIG. 12 is a graph illustrating post-masking.

FIG. 12 illustrates the level characteristics LT of the masked threshold of a Gaussian impulse with a duration of 20 μs as the test tone that is present at a time $t_V$ after the end of a rectangular-shaped masker including white noise with a duration of 500 ms, where the sound pressure level LWR of the white noise takes on the three levels 40 dB, 60 dB and 80 dB. The post-masking of the masker comprising white noise can be measured without spectral effects, since the Gaussian-shaped test tone with a short duration of 20 μs in relation to the perceivable frequency range of the human ear also demonstrates a broadband spectral distribution similar to that of the white noise. The continuous curves in FIG. 12 illustrate the characteristic of the post processing determined by measurements.

They in turn reach the value for the minimum audible threshold of the test tone (about 40 dB for the short test tone used in this case) after about 200 ms, independently of the level LWR of the masker. FIG. 12 shows curves by dotted lines that correspond to an exponential falling away of the post-masking with a time constant of 10 ms. It can be seen that a simple approximation of this kind can only hold true for large levels of the masker, and that it never reflects the characteristic of the post-masking in the vicinity of the minimum audible threshold.

Figure 13:
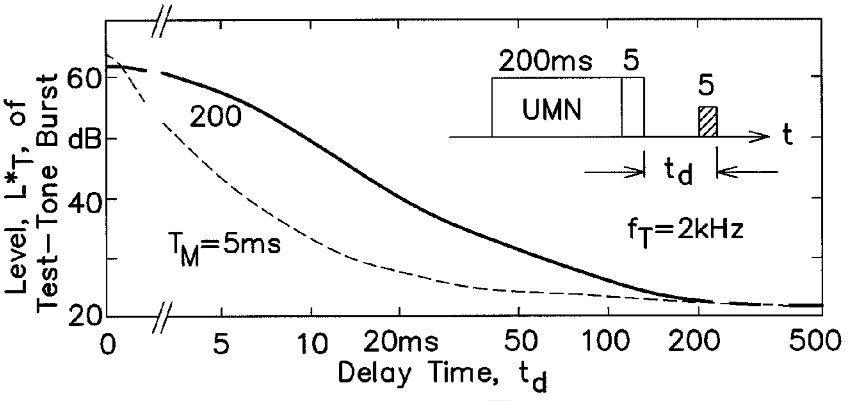
FIG. 13 is a graph illustrating post-masking in relation to the duration of the masker.

A relationship between the post-masking and the duration of the masker is also known. The dotted line in FIG. 13 shows the masked threshold of a Gaussian-shaped test tone impulse with a duration of 5 ms and a frequency of $f_T$=2 kHz as a function of the delay time $t_d$ after the deactivation of a rectangular-shaped modulated masker comprising uniform masking noise with a level LUMN=60 dB and a duration $T_M$=5 ms. The continuous line shows the masked threshold for a masker with a duration of $T_M$=200 ms with parameters that are otherwise identical for test tone impulse and uniform masking noise.

The measured post-masking for the masker with the duration $T_M$=200 ms matches the post-masking also found for all maskers with a duration $T_M$ longer than 200 ms but with parameters that are otherwise identical. In the case of maskers of shorter duration, but with parameters that are otherwise identical (like spectral composition and level), the effect of post-masking is reduced, as is clear from the characteristics of the masked threshold for a duration $T_M$=5 ms of the masker. To use the psychoacoustic masking effects in algorithms and methods, such as the psychoacoustic masking model, it also has to be known what resulting masking is obtained for grouped, complex or superimposed individual maskers.

Simultaneous masking exists if different maskers occur at the same time. Only few real sounds are comparable to a pure sound, such as a sinus tone. In general, the tones emitted by musical instruments, as well as the sound arising from rotating bodies, such as engines in automobiles, have a large number of harmonics. Depending on the composition of the levels of the partial tones, the resulting masked thresholds can vary greatly.

Figure 14:
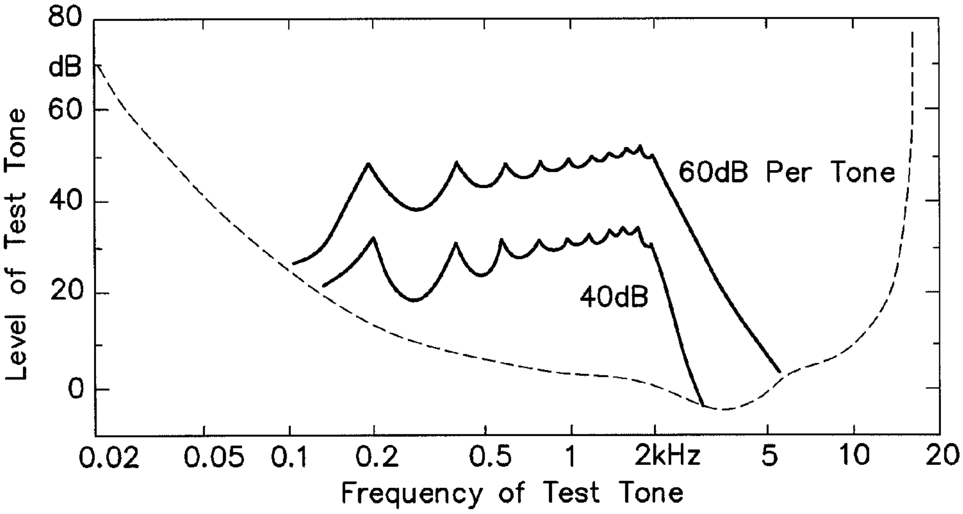
FIG. 14 is a graph illustrating simultaneous masking by a complex audio signal.

FIG. 13 shows the resulting masked thresholds for two cases in which all levels of the partial tones are either 40 dB or 60 dB. The fundamental tone and the first four harmonics are each located in separate frequency groups, meaning that there is no additive superimposition of the masking parts of these complex sound components for the maximum value of the masked threshold. FIG. 14 shows the simultaneous masking for a complex sound. The masked threshold for the simultaneous masking of a sinus-shaped test tone is represented by the ten harmonics of a 200-Hz sinus tone in relation to the frequency and level of the excitation. All harmonics have the same sound pressure level, but their phase positions are statistically distributed.

However, the overlapping of the upper and lower edges and the depression resulting from the addition of the masking effects, which at its deepest point is still considerably higher than the minimum audible threshold, can be clearly seen. All other spectral components of a sound located below this compiled masked threshold cannot be perceived by the human ear and make no contribution, for example, to a noisy impression of these components. In contrast, most of the upper harmonics are, as shown in FIG. 14, within a critical bandwidth of the human hearing. A strong additive superimposition of the individual masked thresholds takes place in this critical bandwidth.

As a consequence of this, the addition of simultaneous maskers cannot be calculated by adding their intensities together, but instead the individual specific loudness values are added together to define the psychoacoustic model of masking.

To obtain the excitation distribution from the audio signal spectrum of time-varying signals, the known characteristics of the masked thresholds of sinus tones for masking by narrowband noise are used as the basis of the analysis. A distinction is made here between the core excitation (within a critical bandwidth) and edge excitation (outside a critical bandwidth). An example of this is the psychoacoustic core excitation of a sinus tone or a narrowband noise with a bandwidth smaller than the critical bandwidth matching the physical sound intensity. Otherwise, the signals are correspondingly distributed between the critical bandwidths masked by the audio spectrum.

In this way, the distribution of the psychoacoustic excitation is obtained from the physical intensity spectrum of the received time-variable sound. The distribution of the psychoacoustic excitation is referred to as the specific loudness. The resulting overall loudness in the case of complex audio signals is found to be an integral over the specific loudness of all psychoacoustic excitations in the audible range along the tonal scale, i.e., in the range from 0 to 24 barks, and also exhibits corresponding time relations. Based on this overall loudness, the masked threshold is then created on the basis of the known relationship between loudness and masking, whereby the masked threshold drops to the minimum audible threshold in about 200 ms under consideration of time effects after termination of the sound within the relevant critical bandwidth (see also FIG. 12, post-masking).

In this way, the psychoacoustic masking model is implemented under consideration of all masking effects discussed above. It can be seen from the preceding what masking effects are caused by sound pressure levels, spectral compositions and timing characteristics of noises, such as background noise, and how these effects can be utilized to reduce the information content of a signal using smoothing in the time and frequency domains without corrupting the resulting perceived impression. It is clear that a signal with less informational content in the time and frequency domains can be analyzed with reduced computing requirements in a digital signal processor to obtain an estimate of the power spectral density.

To further reduce the computing requirements of the algorithm it is also useful not to process the individual spectral components of the signal, but to compile the excitation patterns that occur in individual critical bandwidths or frequency groups. As explained above, the basis of the critical bandwidth is that the human ear groups sounds together that arise in particular frequency ranges as a common aural impression regarding the psychoacoustic impressions of the sounds, where the scope of the aural impression can be covered by 24 successively arranged frequency groups.

If advantage is taken of the fact that voice signals do not cover the entire frequency range of acoustic perception with regard to their spectral distribution, frequency groups can be defined in which no corruption is to be expected due to the simultaneous presence of voice signals. Other algorithms (for example, simpler algorithms with fewer processing requirements) can be used for these frequency groups to estimate the power spectral density, or subsequent filtering can be generally implemented for these sub bands without any previous estimation of the power spectral density. The frequency range of human speech typically extends from 60 Hz to 8 kHz, where the stated upper and lower limits are only reached in extreme cases and at very low levels.

It can be seen from the above that the stated methods and systems, particularly smoothing over time and frequency based on the psychoacoustic perception, can be applied individually or in different combinations in accordance with the characteristics of the background noise and the general situation in order to obtain, on the one hand, the desired result, a reliable estimate of the power spectral density of the background noise without corruption by voice signals, and, on the other hand, to strongly reduce the required computing power for implementation on digital signal processors, so that costs can be reduced.

An advantageous effect is obtained particularly from the adaptive modification of the control time constants in the algorithm for estimating the power spectral density of the background noise. These control time constants increase the increments or decrements in increasing steps within defined maximum limits in the algorithm for approximation of the estimated power spectral density of the background noise to the actual level of the power spectral density of the background noise whenever the currently measured value of the power spectral density of the background noise continually exceeds or undershoots the estimate value of the power spectral density of the background noise in successive computational steps of the algorithm. Thereby superior consideration of fast changes in level of the background noise is enabled compared to known methods, for example, in the estimation of the power spectral density without interference due to a voice signal.

Further advantages can be obtained if the method does not derive the increments or decrements in the algorithm for approximation of the estimated power spectral density of the background noise to the actual level of the power spectral density of the background noise from the characteristic of the overall level of the power spectral density throughout the whole frequency domain. Rather the method refers to the individual spectral components of the power spectral density so that the different pattern of changes in level of the background noise is considered at various spectral positions.

Even more benefits can be seen if the measured power spectral density of the background noise is smoothed both in the time and frequency domains before making the estimation under consideration of the psychoacoustic concealment effects of the human ear. This, by including the psychoacoustic masking in the time and frequency domains, yields a strong reduction in the number of spectral lines to be measured regarding level changes for the estimation of the power spectral density. Therefore, this approach requires considerably less computing power.

Additional advantages can be derived if the control time constants for the increments or decrements in the algorithm for approximation of the estimated power spectral density of the background noise are not determined for each individual spectral line in the power spectral density from the smoothed signal, but rather for a small number of frequency bands, which correspond to the frequency groups in which the human ear compiles sonic activity and, for example, uses for composing the perceived loudness, which consequently again requires less computing power in comparison to the analysis of individual spectral components in the smoothed signal. This is achieved by merging spectral components present in each one of consecutive frequency groups covering the frequency range of interest into a single combined signal representative for the spectral content of each of those frequency groups.

Although various examples to realize the invention have been disclosed, it will be apparent to those skilled in the art that various changes and modifications can be made which will achieve some of the advantages of the invention without departing from the spirit and scope of the invention. It will be obvious to those reasonably skilled in the art that other components performing the same functions may be suitably substituted. Such modifications to the inventive concept are intended to be covered by the appended claims.

What is claimed is:

1. A system for estimating the power spectral density of acoustical background noise, the system comprising:

- a sensor unit for generating a noise signal representative of the background noise;
- a power spectral density calculation unit that is determines the current power spectral density of the noise signal provides a power spectral density output signal indicative thereof;
- a time domain signal smoothing unit that smoothes the power spectral density output signal in the time domain and provides a resulting timely smoothed signal indicative thereof;
- a frequency domain signal smoothing unit that smoothes the timely smoothed signal in the frequency domain and provides a resulting smoothed power spectral density signal indicative thereof;
- an increment calculation unit that calculates an increment value depending the power spectral density output signal;
- a decrement calculation unit that calculates of a decrement value depending on the power spectral density output signal;
- an estimate signal smoothing unit that receives the smoothed power spectral density signal, the increment value and the decrement value and provides an estimated calculation power spectral density of the background noise; where
- for cases in which the level of the smoothed power spectral density signal increases, the increment value is increased, starting from a minimum increment value, by a predetermined amount until a maximum increment value is reached if at the same time the value of the power spectral density currently determined in a new calculation cycle is larger than the estimate value of the power spectral density of the background noise determined in the previous calculation cycle; and
- for cases in which the level of the smoothed power spectral density decreases, the decrement value is increased, starting from a minimum decrement value, by a predetermined amount until a maximum decrement value is reached if at the same time the value of the power spectral density currently determined in a new calculation cycle is smaller than the estimate value of the power spectral density of the background noise determined in the previous calculation cycle.

2. The system of claim 1, further comprising an adaptive filter that provides an error signal, where the power spectral density calculation unit determines the power spectral density from the error signal deploying consecutive calculation cycles and the system is adapted to provide a corresponding power spectral density output signal and a corresponding smoothed power spectral density signal.

3. The system of claim 2, where the system changes the calculation for estimating the power spectral density of the background noise from the mode for calculation of the increment value to the mode for calculation of the decrement value if the value of the power spectral density determined in a current calculation cycle is less than the estimate value of the power spectral density of the background noise calculated in the previous calculation cycle, where the system is adapted for resetting the current value of the increment value to the minimum increment value, and

- to change the calculation for estimating the power spectral density of the background noise from the mode for calculation of the decrement value to the mode for calculation of the increment value if the value of the power spectral density determined in the current calculation cycle is greater than the estimate value of the power spectral density of the background noise calculated in the previous calculation cycle, where the system is adapted for resetting the current value of the decrement to the minimum decrement value.

4. The system of claim 1, where the estimated signal calculation unit limits the reduction of the estimated power spectral density value to a fixed specified value, such that the estimated power spectral density does not fall below the minimum value regardless of the currently calculated value.

5. The system of claim 1, where the time domain signal smoothing unit utilizes two different time constants, one for the case of a rising signal and one for the case of a falling signal.

6. The system of claim 5, where the frequency domain signal smoothing unit smoothes the timely smoothed signal, starting from a minimum frequency upward using a frequency smoothing third coefficient, and/or starting from a maximum frequency downward, using a frequency smoothing fourth coefficient.

7. The system of claim 6, where the first and second coefficients for smoothing over time of the currently measured power spectral density represent psychoacoustic sensory properties of the human ear; and the third and fourth coefficients for smoothing over frequency of the currently measured power spectral density represent psychoacoustic sensory properties of the human ear.

8. The system of claim 1, where the value for the increase of the increment value is individually selected with values differing for each spectral position in the smoothed power spectral density signal of the currently measured power spectral density and where the value for the increase of the decrement value is individually selected with values differing for each spectral position in the smoothed power spectral density signal of the currently measured power spectral density.

9. The system of claim 1, wherein the system is adapted to merge spectral components of the smoothed or non-smoothed power spectral density signal within frequency groups corresponding to the psychoacoustic sensory perception into single combined signals for each frequency group prior to further processing.

10. A method for estimation of the power spectral density of acoustical background noise, comprising the steps of:

determining the current power spectral density from a microphone signal and providing a power spectral density output signal;

smoothing the power spectral density output signal in the time domain and providing a timely smoothed signal;

smoothing the timely smoothed signal in the frequency domain and providing a smoothed power spectral density signal;

calculating an increment value depending on an estimate value of a power spectral density of the background noise;

calculating a decrement value depending on the estimate value of the power spectral density of the background noise;

calculating an estimate value of the power spectral density of the background noise from the increment value and decrement value, where for cases in which the level of the smoothed power spectral density signal increases, the increment value is increased, starting from a minimum increment value, by a predetermined amount until a maximum increment value is reached if at the same time the value of the power spectral density currently determined in a new calculation cycle is larger than the estimate value of the power spectral density of the background noise determined in the previous calculation cycle, and for cases in which the level of the smoothed power spectral density decreases, the decrement value is increased, starting from a minimum decrement value, by a predetermined amount until a maximum decrement value is reached if at the same time the value of the power spectral density currently determined in a new calculation cycle is smaller than the estimate value of the power spectral density of the background noise determined in the previous calculation cycle.

11. The method of claim 10, further comprising the step of:

determining the current power spectral density from an error signal derived from adaptive filtering by deploying consecutive calculation cycles; and providing a corresponding power spectral density output signal and a corresponding smoothed power spectral density signal.

12. The method of claim 10, further comprising the steps of:

changing the calculation for estimating the power spectral density of the background noise from the mode for calculation of the increment value to the mode for calculation of the decrement value if the current value of the power spectral density determined in a new calculation cycle is less than the estimate value of the power spectral density of the background noise calculated in the previous calculation cycle, where the current value of the increment value is reset to the minimum increment value, and changing the calculation for estimating the power spectral density of the background noise from the mode for calculation of the decrement value to the mode for calculation of the increment value if the current value of the power spectral density determined in a new calculation cycle is greater than the estimate value of the power spectral density of the background noise calculated in the previous calculation cycle, where the current value of the decrement is reset to the minimum decrement value.

13. The method of claim 10, further comprising the step of limiting, in the event of decrementing the estimate value of the power spectral density, the reduction of the estimate value to a fixed specified value, such that the estimate value does not fall below the minimum value regardless of the currently calculated value.

14. The method of claim 10, where the step of smoothing the power spectral density output signal utilizes two different time constants, one for the case of a rising signal and one for the case of a falling signal.

15. The method of claim 14, where the step of smoothing the timely smooth signal, comprises starting from a minimum frequency upward using a frequency smoothing third coefficient, or starting from a maximum frequency downward, using a frequency smoothing fourth coefficient.

16. The method of claim 15, where the first and second coefficients for smoothing over time of the currently measured power spectral density re-present psychoacoustic sensory properties of the human ear, and/or the third and fourth coefficients for smoothing over frequency of the currently measured power spectral density represent psychoacoustic sensory properties of the human ear.

17. The method of claim 16, where the value for the increase of the increment value is individually selected with values differing for each spectral position in the smoothed power spectral density signal of the currently measured power spectral density and where the value for the increase of the decrement value is individually selected with values differing for each spectral position in the smoothed power spectral density signal of the currently measured power spectral density.

18. The method of claim 10, where spectral components of the smoothed power spectral density signal within frequency groups corresponding to the psychoacoustic sensory perception are merged into single combined signals for each frequency group prior to further processing.

* * * * *